(12) United States Patent
Haje

(10) Patent No.: US 6,250,919 B1
(45) Date of Patent: Jun. 26, 2001

(54) DENTAL BRIDGE HOLDER ALIGNMENT MECHANISM

(76) Inventor: Emad El Haje, 1800 Eye St., Suite 402, Washington, DC (US) 20006

( * ) Notice: Subject to any disclaimer, the term of this patent is extended or adjusted under 35 U.S.C. 154(b) by 0 days.

(21) Appl. No.: 09/495,295

(22) Filed: Feb. 1, 2000

(51) Int. Cl.$^7$ ...................................................... A61C 3/00
(52) U.S. Cl. .............................................. 433/50; 433/75
(58) Field of Search ................................. 433/49, 50, 51, 433/55, 56, 60, 72, 75, 76

(56) References Cited

U.S. PATENT DOCUMENTS

| | | | |
|---|---|---|---|
| 2,095,665 | * | 10/1937 | Greth . |
| 3,760,504 | * | 9/1973 | Ljubarsky et al. . |
| 4,007,531 | * | 2/1977 | Anderson . |
| 4,023,275 | * | 5/1977 | Marshall . |
| 4,205,445 | * | 6/1980 | Tzeng ...................................... 433/50 |
| 4,624,639 | * | 11/1986 | Wong ....................................... 435/56 |
| 4,840,564 | * | 6/1989 | Segal ....................................... 433/72 |
| 5,064,368 | * | 11/1991 | Lavin ....................................... 433/53 |
| 5,551,873 | * | 9/1996 | Aiba ........................................ 433/72 |
| 6,186,781 | * | 2/2001 | IBA ......................................... 433/50 |

* cited by examiner

Primary Examiner—Ralph A. Lewis
(74) Attorney, Agent, or Firm—Barnes & Thornburg

(57) ABSTRACT

A dental impression alignment device comprising a support; a support table for supporting a dental impression mounted to said support by a universal joint; an index rod attached to said support to extend adjacent the support table for providing a reference plane for orienting the impression and support table relative to the support; and a drill guide attached to either said support or said index rod for providing a drill aligning structure to provide a drill axis for drilling a reference channel in the impression which channel has an axis fixed with respect to the index rod.

32 Claims, 2 Drawing Sheets

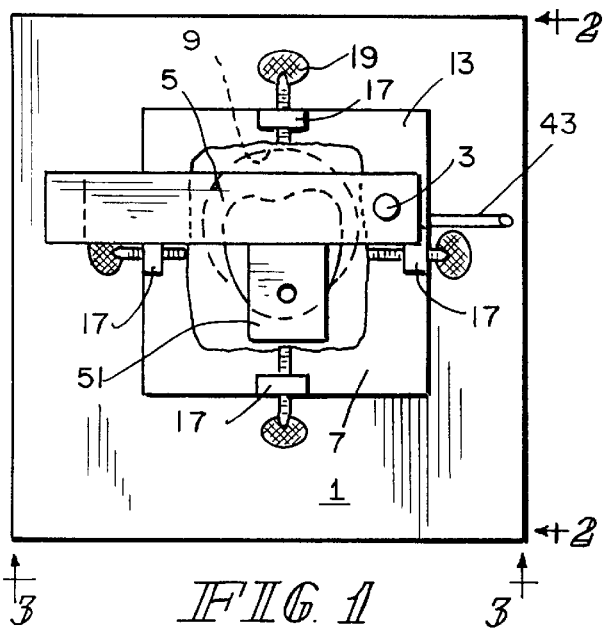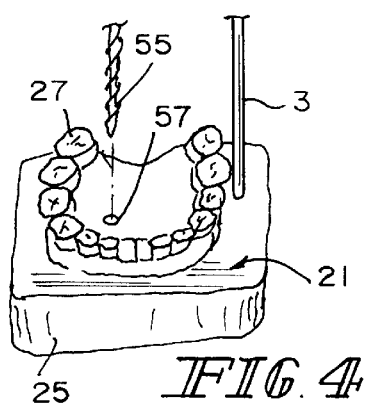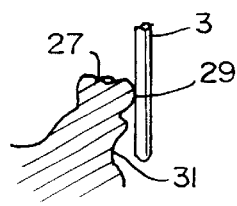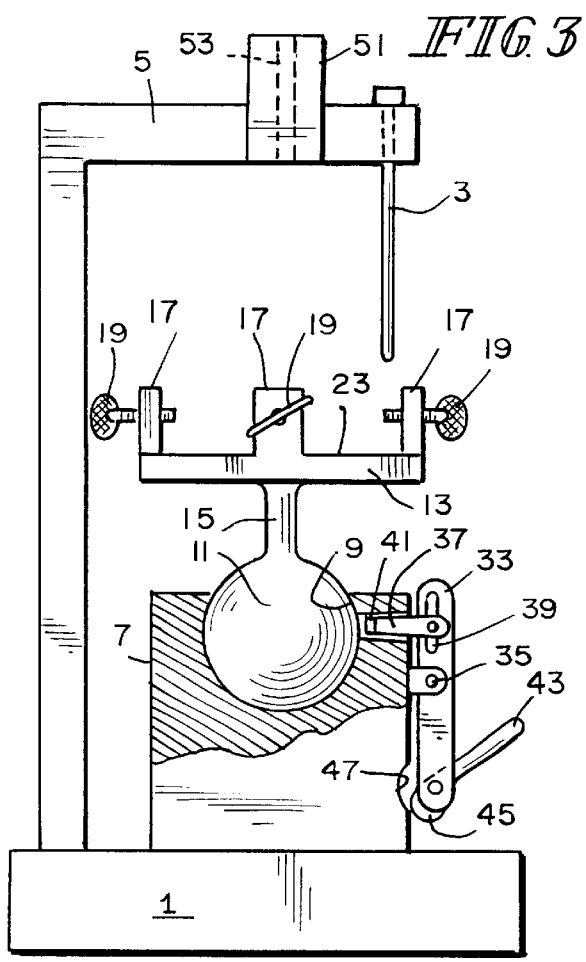

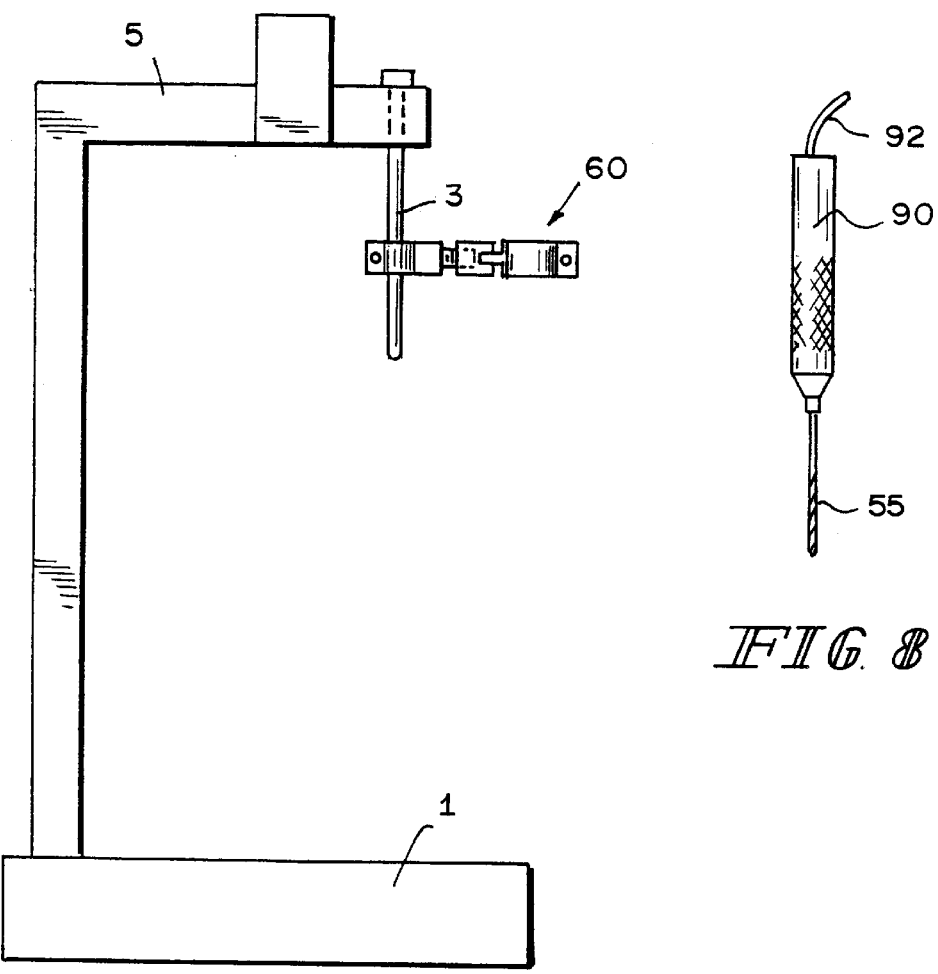
FIG. 6
FIG. 8
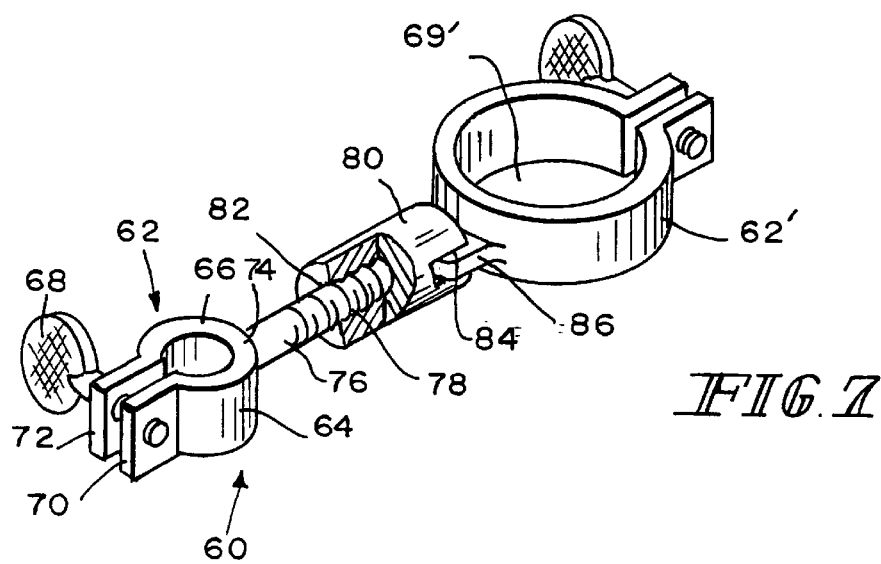
FIG. 7

DENTAL BRIDGE HOLDER ALIGNMENT MECHANISM

BACKGROUND OF SUMMARY OF INVENTION

The invention relates to an indexing device and method for reproducing the axis of a universal joint mounted dental impression holder.

In the making of partial bridges, the dentist reviews the patient's teeth impressions to determine the patient's best natural teeth to use for the surface attachment of the clips of a partial bridge. The method to determine the best natural teeth involves taking the patient's impression and securing it to a support table by mounting clamps. The mounting clamps are located on the support table which is attached to a support stand by a universal joint to allow the dentist freedom to move an impression secured by the mounting clamps to the support table relative to an index rod that is supported by the support stand. By angularly adjusting the support table with respect to the index rod, the teeth profiles with the greatest curvature are easily determined and can be marked. The impression is then sent to a dental laboratory where the dental bridge is made.

An alignment problem exists at the laboratory. While the attachment teeth are known by the markings, reproduction of the angularity of the support table at the laboratory to that used by the dentist can only be approximated.

The instant invention provides an indexing method and apparatus whereby the angularity of the support table of the dentist can be exactly reproduced at the laboratory.

The reproduction is made possible by the dentist drilling an alignment hole in the impression when the desired orientation of the impression and the index rod is obtained. The orientation of a drilling guide and the index rod are fixed and parallel to one another. Knowing this relationship and having a duplicate orientation mechanism at the laboratory allows the technician at the laboratory to insert a positioning rod into the drill holder of the laboratory support mechanism and the drilled hole in the impression to thus replicate the angle used by the dentist.

To accomplish the alignment method, a drill guide alignment arm is fixedly attached to the index rod, or the support arm for the index rod. The alignment arm is provided with a drill guide hole that extends parallel to the index rod. When the dentist finds the desired orientation of the impression with respect to the index arm, the support table is clamped to prohibit movement. A drill is then inserted into the drill guide and is used to drill an alignment hold into the impression.

When the impression reaches the laboratory, it is clamped onto the laboratory support table and oriented to a position where an alignment rod, that is inserted into the drill guide hole, can enter into the hole that the dentist previously drilled in the impression. At that point, the orientation of the technician's support table and that of the dentist is the same. Accordingly, the technician no longer has to worry about approximating the dentist's orientation.

BRIEF DESCRIPTION OF THE DRAWINGS

FIG. 1 is a plan view of the dentist's positioning apparatus;

FIG. 2 is an end view of the dentist's positioning apparatus taken along the plane 2—2 of FIG. 1;

FIG. 3 is a side view of the dentist's positioning apparatus taken along the plane 3—3 of FIG. 1 and with the support cage for the universal mounting of the support table shown partially in section;

FIG. 4 shows the alignment rod, index rod and impression at the dentist laboratory;

FIG. 5 shows how the dentist orients the impression with respect to the index rod.;

FIG. 6 shows a preferred embodiment where the drill guide is attached to the index rod;

FIG. 7 shows details of the drill guide of FIG. 6; and

FIG. 8 shows a dental drill.

DETAILED DESCRIPTION OF THE DRAWINGS

The known orientation mechanism for a dentist to use in determining the teeth to be captured by clips of a partial bridge is shown in FIGS. 1–3 and consists of a support stand 1, an index rod 3, attached to an index rod support arm 5 attached adjacent an edge of the support stand 1 to extend upwardly and over the support stand 1. The index rod 3 need not be a rod but could be a plate or other fixed structure that can be used for alignment purposes. The use of the term "rod" is to cover all these equivalences. A universal ball joint mount 7 is fixedly attached to the support stand 1 and has a semispherical opening 9 to receive a ball 11 of the universal joint. The ball 11 is fixedly attached to an impression support table 13 via a stem member 15. The support table 13 has a series of upwardly extending impression clamp legs 17 provided with twist screws 19 to hold a dental impression 21 (FIG. 4) on the flat upper surface 23 of the support table 13. The impression is placed on the flat surface 23 and the screws 19 rotated inwardly to clamp against the four sides 25 of the impression 21. The impression has individual teeth shapes 27 therein. The contours of the teeth have outwardly extending bulbous portions 29 and recess portions 31 (FIG. 5). To determine the location of the clips on a partial denture, the impression (after mounting on the support table 13) is oriented with respect to the depending index rod 3 until an ideal tooth with bulbous portion 29 and recess 31 is located. The support table is free to rotate about spherical socket 9. The index rod 3 provides the dentist with a clear relative image of the amount of bulbous tooth portion 29 and recess 31 to allow for proper tooth selection.

Once the proper orientation of the support table is determined by the dentist comparing the tooth profiles against the index rod 3, the ball 11 of the universal joint is clamped in position. One type of clamp could be a clamp arm 33 pivotally mounted to the universal ball joint mount 7 by support arm 35. At the upper end of clamp arm 33, a clamp rod 37 is pivotally mounted in slot 39. An inner rod end of the clamp arm has a rubber tip 41. The lower end of the clamp arm has a crank 43 rotatably mounted thereon. Attached to the crank 43 is a rotating cam 45 which operates against an indented cam surface 47 in the ball joint mount 7. Rotation of the handle clockwise (as shown in FIG. 3) causes the cam 45 to engage the cam surface 47 and pushes the lower end of the clamp arm 33 away from the ball joint mount 7. The clamp arm 33 pivots about support arm 35 to cause the clamp rod to move inwardly of the ball joint mount 7 wherein the rubber tip 41 engages and stops the ball 11 from moving.

The particular type of clamping mechanism for the ball 11 is not critical. The ball mount could be in the form of two clam shells that could be clamped together to hold a ball there between. There could be a high co-efficient of friction between the ball and the spherical recess 9 that would hold the ball stationary. While a ball joint is shown, other types of universal joints could be used such as the two axis type found in automobile drive shafts.

What is important is that the support table 13 be free to move universally to allow the dentist to properly align the impression 21 with the index rod 3.

The above general structure and equivalences are old and well known as dental equipment. Its use has caused problems in that when the dentist finds the proper orientation and selects and marks the tooth for the clip, the dentist releases the screws 19 and sends the impression 21 to the laboratory to make the partial bridge. The technician will know the tooth, but does not know the actual angles of inclination of the support table 13.

The present invention provides a way for the technician to replicate the angle of the dentist's support table 13. The invention provides an orientation arm 51 fixedly attached, or made integral to the known support arm 5. The orientation arm 51 has a drill guide with a drill guide bore 53 therein. When the proper orientation of the impression 21 is obtained and the ball 11 is clamped to stop movement, a drill bit 55 (see FIG. 4) is inserted into the bore 53 and a hole 57 is drilled in the impression 21. The bore 53 is long enough to keep the drill bit 55 in alignment with the index rod 3. While the hole 57 is shown large enough for reception of the drill bit 55, it could be larger to accommodate the drill body of a normal dentist drill.

A preferred embodiment of the invention would have the drill guide of FIGS. 1–3 not be mounted directly to the index rod support arm 5, but rather to have it mounted to the index rod 3. FIG. 6 shows such a preferred embodiment where a drill support 60 is releasable mounted to the index rod.

FIG. 7 shows the details of the drill support 60 of FIG. 6. At the left end of the drill support is a clamp 62 having two semi-circular arms 64 and 66, which define an opening 69 there between. The index rod 3 can fit within the opening 69 and the two semi-circular arms 64 and 66 can clamp around the rod 3 by means of a screw 68 which pulls the two free ends 70, 72 of the semi-circular arms 64 and 66 together to reduce the opening 69 to tighten the semi-circular arms 64 and 66 against the index rod 3 inserted therein. The two semi-circular arms 64 and 66 are joined at 74 to form a post 76 that has a threaded end 78. A collar 80 (shown partial in section in FIG. 7) screws on to the threaded end 78. The collar 80 has an opening 84 into which is secured a rotating end post 86 of a second clamp 62'. The clamp 62' is structured similar to the clamp 62 except that the aperture 69' is larger so as to be able to receive the body 90 of a dentist's drill (FIG. 8) provided with a source of power (air) via hose 92. The drill 90 also has a drill bit 55. Embodied in the thread 78 is a ruler 82. Rotation of collar 80 about the threaded post 76 elongates or shortens the length of the drill support 60. The ruler 82 will be partially covered by the end as of the collar 80 to indicate the length of the drill support 60. The clamp 62 for the drill itself could be provided with a "TEFLON" insert to allow for easy insertion of the drill 90. The rotating end post 86 allows for the drill clamp 61 to be mounted horizontal while the collar is threaded on the threaded post 78.

While a threaded post 78 is disclosed, any type of telescopic device could be used including interconnecting rectangular or square rods and collars. If friction is used to hold the collar onto a post, a clamp screw could be provided to hold the length and secure the two telescopic members.

When the impression 21 gets to the laboratory, the technician clamps the impression 21 to his support table 13 and moves his ball to the position where an index pin moveable upwards and downwards in the bore on the dentist's mechanism aligns and enters the hole 57 drilled by the dentist.

In this manner an exact replication of impression at the laboratory is obtained.

Although the present invention has been described and illustrated in detail, it is to be clearly understood that the same is by way of illustration and example only, and is not to be taken by way of limitation. The spirit and scope of the present invention are to be limited only by the terms of the appended claims.

What is claimed:

1. A dental impression alignment device comprising:

a support;

a support table for supporting a dental impression mounted to said support by a universal joint;

an index rod attached to said support to extend adjacent the support table for providing a reference plane for orienting the impression and support table relative to the support; and a drill guide attached to one of said support and said index rod for providing a drill aligning structure to provide a drill axis for drilling a reference channel in the impression which channel has an axis fixed with respect to the index rod.

2. The alignment device of claim 1, wherein a clamp is provided for the universal joint to hold the support table at a desired angularity with the index rod.

3. The alignment device of claim 1, wherein the index rod is attached to the support by a support arm attached to the support and wherein the support arm in part extends over the support table and the index arm depends from that portion of the support arm that extends over the support table.

4. The alignment device of claim 2, wherein the index rod is attached to the support by a support arm attached to the support and wherein the support arm in part extends over the support table and the index arm depends from that portion of the support arm that extends over the support table.

5. The alignment device of claim 1, wherein the drill aligning structure is provided with an elongated aperture which guides one of a dental drill or dental drill bit to provide the axis for drilling the reference channel.

6. The alignment device of claim 2, wherein the drill aligning structure is provided with an elongated aperture which guides one of a dental drill or dental drill bit to provide the axis for drilling the reference channel.

7. The alignment device of claim 3, wherein the drill aligning structure is provided with an elongated aperture which guides one of a dental drill or dental drill bit to provide the axis for drilling the reference channel.

8. The alignment device of claim 4, wherein the drill aligning structure is provided with an elongated aperture which guides one of a dental drill or dental drill bit to provide the axis for drilling the reference channel.

9. The alignment device of claim 1, wherein the index rod extends adjacent the support table at a fixed angle with respect to the support and wherein the axis of the drilling channel is parallel to the fixed angle of the index rod with respect to the support.

10. The alignment device of claim 2, wherein the index rod extends adjacent the support table at a fixed angle with respect to the support and wherein the axis of the drilling channel is parallel to the fixed angle of the index rod with respect to the support.

11. The alignment device of claim 3, wherein the index rod extends adjacent the support table at a fixed angle with respect to the support and wherein the axis of the drilling channel is parallel to the fixed angle of the index rod with respect to the support.

12. The alignment device of claim 4, wherein the index rod extends adjacent the support table at a fixed angle with respect to the support and wherein the axis of the drilling channel is parallel to the fixed angle of the index rod with respect to the support.

13. The alignment device of claim 5, wherein the index rod extends adjacent the support table at a fixed angle with respect to the support and wherein the axis of the drilling channel is parallel to the fixed angle of the index rod with respect to the support.

14. The alignment device of claim 6, wherein the index rod extends adjacent the support table at a fixed angle with respect to the support and wherein the axis of the drilling channel is parallel to the fixed angle of the index rod with respect to the support.

15. The alignment device of claim 7, wherein the index rod extends adjacent the support table at a fixed angle with respect to the support and wherein the axis of the drilling channel is parallel to the fixed angle of the index rod with respect to the support.

16. The alignment device of claim 8, wherein the index rod extends adjacent the support table at a fixed angle with respect to the support and wherein the axis of the drilling channel is parallel to the fixed angle of the index rod with respect to the support.

17. The alignment device of claim 7 wherein there is an adjustment device to vary the distance between the axis of the drilling channel and the index rod.

18. The alignment device of claim 8 wherein there is an adjustment device to vary the distance between the axis of the drilling channel and the index rod.

19. The alignment device of claim 9 wherein there is an adjustment device to vary the distance between the axis of the drilling channel and the index rod.

20. The alignment device of claim 10 wherein there is an adjustment device to vary the distance between the axis of the drilling channel and the index rod.

21. The alignment device of claim 11 wherein there is an adjustment device to vary the distance between the axis of the drilling channel and the index rod.

22. The alignment device of claim 12 wherein there is an adjustment device to vary the distance between the axis of the drilling channel and the index rod.

23. The alignment device of claim 13 wherein there is an adjustment device to vary the distance between the axis of the drilling channel and the index rod.

24. The alignment device of claim 14 wherein there is an adjustment device to vary the distance between the axis of the drilling channel and the index rod.

25. The alignment device of claim 15 wherein there is an adjustment device to vary the distance between the axis of the drilling channel and the index rod.

26. The alignment device of claim 16 wherein there is an adjustment device to vary the distance between the axis of the drilling channel and the index rod.

27. A method for replicating, at a remote location, a desired orientation of a dental impression made by a dentist comprising the steps of:

securing a dental impression to a support table attached to a support via a universal joint;

aligning the impression and support table with respect to an index rod attached to the support at a fixed angle to extend adjacent the support table; and drilling a reference channel in the impression after alignment, which reference channel has an axis fixed with respect to the position of the index rod.

28. The method of claim 27, wherein the drilling step is occasioned by inserting a drill in a drill guide attached to one of the support and the index rod.

29. The method of claim 27, wherein the axis of the reference channel is parallel to a surface of the index rod.

30. The method of claim 28, wherein the axis of the reference channel is parallel to a surface of the index rod.

31. The method of claim 29 wherein the distance between the axis of the reference channel and the surface of the index rod can be changed.

32. The method of claim 30 wherein the distance between the axis of the reference channel and the surface of the index rod can be changed.

* * * * *